United States Patent [19]
Harboe et al.

[11] Patent Number: 6,127,142
[45] Date of Patent: Oct. 3, 2000

[54] MICROBIALLY DERIVED ENZYMES HAVING ENHANCED MILK CLOTTING ACTIVITY AND METHOD OF PRODUCING SAME

[75] Inventors: Marianne Kirsten Harboe, Lyngby; Pia Bach Kristensen, Glostrup, both of Denmark

[73] Assignee: Chr. Hansen A/S, Horsholm, Denmark

[21] Appl. No.: 08/849,922

[22] PCT Filed: Dec. 20, 1995

[86] PCT No.: PCT/DK95/00511

§ 371 Date: Aug. 14, 1997

§ 102(e) Date: Aug. 14, 1997

[87] PCT Pub. No.: WO96/19582

PCT Pub. Date: Jun. 27, 1996

[30] Foreign Application Priority Data

Dec. 21, 1994 [DK] Denmark .................. 1459/94

[51] Int. Cl.$^7$ .............. C12P 21/06; C12N 9/58; A23C 9/12
[52] U.S. Cl. .............. 435/68.1; 435/69.1; 435/223; 426/40; 426/42
[58] Field of Search ................ 435/68.1, 69.1, 435/223; 426/40, 42

[56] References Cited

U.S. PATENT DOCUMENTS

| | | | |
|---|---|---|---|
| 3,763,010 | 10/1973 | Schleich ................................. | 195/63 |
| 4,348,482 | 9/1982 | Cornelius ............................. | 435/223 |
| 4,853,329 | 8/1989 | Havera et al. ...................... | 435/183 |
| 5,171,673 | 12/1992 | Sloma et al. ....................... | 435/69.1 |

FOREIGN PATENT DOCUMENTS

| | | |
|---|---|---|
| 0179449 | 10/1985 | European Pat. Off. . |
| 0238023 | 3/1987 | European Pat. Off. . |
| 3827087 | 8/1988 | Germany . |
| 8907641 | 8/1989 | WIPO . |
| 9424880 | 11/1994 | WIPO . |

OTHER PUBLICATIONS

P.A. McBride–Warren and W.S. Rickert—"Structural and Functional Determinaants of Mucor Mieheiprotease"—Biochimica Et Biophysica Acta, vol. 328 (1973) pp. 52–60.

Tove Christensen, et al. "High Level Expression of Recombinant—Genes in *Aspergillus Oryzae*" Bio/Technology,—vol. 6. (Dec. 1988) pp. 1419–1422.

Gene, vol. 48, 1986, pp. 41–53, G. Gray et al Primary Structure of Mucor Miehie Aspartyl Protease: Evidence for a Zymogen Intermediate.

Molecular & General Genetics 241 (3–4). 1993. 312–318. Murakami et al Characterization of an Aspartic Proteinase of *Mucor Pusillus* Expressed in *Aspergillus Oryzae*.

J. Bacteriol (1994), 176(9), 2635–9 Murakami, Kohji et al "A *Mucor Pusillus* Mutant Defective in Asparagine–Linked Glycosylation".

J. Biol. Chem. (1990), 265(23), 13955–9, Aikawa, Junichi et al "Effects of Glycosylation on the Secretion and Enzyme Activity of Mucor Rennin, an Aspartic Proteinase of *Mucor Pusillus*, Produced by Recombinant Yeast".

Scand. J. Clin. Lab. Invest., Suppl. (1992), 52(210), 51–8, Aikawa, J. et al "Protein Engineering of the Milk–Clotting Aspartic Proteinases".

*Primary Examiner*—Ponnathapu Achutamurthy
*Assistant Examiner*—Peter P. Tung
*Attorney, Agent, or Firm*—Ladas & Parry

[57] ABSTRACT

A method of producing a milk clotting enzyme including the steps of (a) fermenting a strain of *Rhizomucor miehei* or *Aspergillus oryzae* to form a fermentation product having a glycoslated *Rhizomucor miehei* aspartic protease and other proteins, and (b) subjecting a quantity of the fermentation product to a deglycosylating treatment to form a coagulant preparation having an at least partly deglycoslated aspartic protease and the other proteins. The at least partly deglycosylated protease has a milk clotting activity that is at least 10% higher than a milk clotting activity of the glycosylated aspartic protease.

23 Claims, No Drawings

MICROBIALLY DERIVED ENZYMES HAVING ENHANCED MILK CLOTTING ACTIVITY AND METHOD OF PRODUCING SAME

FIELD OF THE INVENTION

The present invention relates to at least partially deglycosylated microbially derived milk clotting enzymes and in particular to aspartic proteases derived from *Rhizomucor miehei* and having improved milk clotting activity.

TECHNICAL BACKGROUND FOR THE INVENTION AND THE PRIOR ART

Milk clotting enzymes are widely used in the cheese manufacturing industry to provide a curd of the major milk proteins. Commercially available milk clotting enzymes include native (or homologous) enzymes derived from microbial species or animal tissue sources such as calf stomachs, or such enzymes can be provided as gene products of recombinant cells expressing a heterologous milk clotting enzyme of animal or microbial origin.

Milk clotting enzymes of microbial origin are in commercial use in the dairy industry. In the following, such enzymes are also referred to as microbial milk clotting enzymes, microbial rennets or microbial coagulants. Examples of such enzymes include proteases natively produced by the zygomycete filamentous fungal species *Rhizomucor miehei* and *Rhizomucor pusillus* and protease produced by the fungal species *Endothia parasitica*. Enzymes having milk clotting activity can also be produced by other microbial species, including Rhizopus species, Physarum species, Penicillium species and Bacillus species.

The major milk clotting enzyme derived from *Rhizomucor miehei* is an aspartic protease (EC 3.4.23) being produced extracellularly by this fungal species and having a relatively high milk clotting activity and a relatively low proteolytic activity, i.e. with a desirable low ratio between proteolytic activity and milk clotting activity. A commercial coagulant containing *Rhizomucor miehei* aspartic protease is also referred to in the industry as a Mucor rennin.

Microbial coagulant compositions may be based on enzymes produced by microbial strains naturally producing milk clotting enzymes (homologous enzymes), or they can be based on enzymes produced by a heterologous strain. Thus, as an example Aikawa et al. 1990, J. Biol. Chem., 265, 13955–13959 have disclosed the expression of the *Rhizomucor pusillus* rennin in a strain of *Saccharomyces cerevisiae*.

One advantage of using a heterologous production strain in the industrial manufacturing of microbial coagulants such as aspartic proteases is that undesirable contamination with other proteases generally occurring in homologously produced enzyme preparations can be at least partially eliminated.

It is well-known that microbially produced enzymes may be glycosylated when expressed, the degree of glycosylation depending on the type of enzyme and the microbial species expressing the enzyme. Thus, Aikawa et al., supra found that the mature *Rhizomucor pusillus* aspartic protease as produced homologously in that species only contained a few glycosidic moieties in its molecules whereas the enzyme, when it was expressed in *Saccharomyces cerevisiae*, was highly glycosylated (about 37 residues/mole). These investigators found that deglycosylation of the heterologous protease which was achieved by treating this milk clotting enzyme with endo-β-N-acetylgalactosaminidase resulted in enhancement of its milk clotting activity, whereas treating the homologously produced protease similarly did not affect the milk clotting activity hereof.

Gray et al., 1986, Gene, 48, 41–53 disclosed expression of *Rhizomucor miehei* aspartic protease in *Aspergillus nidulans* and found that this heterologously produced protease had the same specific activity as determined in a milk turbidity assay as had the corresponding homologously produced protease.

Recently, a commercial *Rhizomucor miehei* derived aspartic protease produced in *Aspergillus oryzae* has been disclosed (Novo Nordisk, Biotimes, June 1994). The milk clotting activity of this heterologous protease was studied by Christensen et al., 1988, Biotechnology, 6, 1419–1422. These authors found that the protease was overglycosylated which, however, according to these authors did not alter the specific activity of the enzyme. In WO 94/24880 it is specifically disclosed that this recombinant aspartic protease has an N-bound glucosamin, galactose and mannose content of 100% more than the corresponding native enzyme.

The above protease is marketed by Novo Nordisk under the trade name Novoren®. In the documentary material which was filed by the manufacturer with the U.S. Food and Drug Administration to obtain approval of its recombinant aspartic protease there are referred to experiments where the enzyme was treated with endoglycosidase H (Endo-H) which caused deglycosylation. It is stated that the extra glycosylation of the heterologously expressed enzyme does not alter the specific activity of the enzyme significantly. Furthermore, in the above Novo Nordisk publication, Biotimes, June 1994 it is stated on page 2 about Novoren® that the manufacturer cannot see how this enzyme preparation can be further improved.

McBride-Warren et al. 1973, Biochimica et Biophysica Acta, 328, 52–60 disclosed that homologous *Rhizomucor miehei* aspartic protease was glycosylated and that the removal of 40–50% of the sugar moieties (deglycosylation) resulted in a loss of up to 50% of the enzymatic activity.

Homologous aspartic protease produced by *Rhizomucor miehei* has been widely used in the dairy industry as a milk clotting enzyme for about 25 years. Examples of commercial products containing this enzyme are Rennilase® marketed by Novo Nordisk and the commercial products Hannilase® and Modilase S® sold by Chr. Hansen A/S.

It has now surprisingly been found that homologous *Rhizomucor miehei* aspartic protease, contrary to what has been stated in the prior art, acquires a significantly enhanced milk clotting activity when it is deglycosylated, and furthermore, that the milk clotting activity of heterologous *Rhizomucor miehei* aspartic protease as produced in *Aspergillus oryzae*, contrary to the above disclosures by a manufacturer hereof, is enhanced significantly by deglycosylation.

SUMMARY OF THE INVENTION

Accordingly, the present invention provides in a first aspect a method of enhancing the milk clotting activity of a glycosylated aspartic protease derived from *Rhizomucor miehei*, said protease being homologously produced or produced in *Aspergillus oryzae*, the method comprising subjecting the protease to a deglycosylating treatment to increase the milk clotting activity of the protease by at least 10%. The protease being subjected to the decosylating treating may be pre-treated by subjecting it to oxidation.

In a further aspect, the present invention pertains to a *Rhizomucor miehei* derived aspartic protease which is produced homologously or in *Aspergillus oryzae* in a glycosylated form, the protease being less glycosylated relative to the form wherein it is produced and having at least 10% higher milk clotting activity than the protease as produced.

In other further aspects, the invention relates to a milk clotting composition comprising the protease as defined above, and at least one additive and to the use of such a protease or a composition comprising the protease in the manufacturing of cheese.

In a still further aspect, the invention relates to a method of producing an aspartic protease derived from *Rhizomucor miehei*, which, when expressed in a naturally occurring, homologous strain is in a glycosylated form, the method comprising isolating the gene or genes coding for the protease and inserting said gene or genes into a homologous or heterologous microbial species capable of expressing said gene or genes without glycosylating the protease or glycosylating it to such a lesser extent relative to the naturally occurring strain that the milk clotting activity of such less glycosylated form of the protease is increased by at least 10%.

DETAILED DISCLOSURE OF THE INVENTION

The method of enhancing the milk clotting activity of a microbial coagulant which, when produced in a microbial strain, occurs in a glycosylated form, may e.g. comprise treating the glycosylated coagulant with an enzyme having a deglycosylating activity including as an example endo-β-N-acetylglucosaminidase (EC 3.2.1.96) (Endo-H).

Furthermore, the method according to the invention encompasses a treatment of the glycosylated coagulant chemically in such a manner that glycosyl moieties are removed from it. As an example, the coagulant can be subjected to a treatment with periodate.

The above treatment according to the invention results in removal of glycosyl moieties to an extent which depends on the degree of glycosylation and, when a deglycosylating enzyme is applied, the amount and the enzymatic activity of the enzyme and on the time of enzyme treatment. As an example, the coagulant produced natively by *Rhizomucor miehei* has three possible N-linked glycosylation sites i.e. sites having the sequence Asn-X-Thr/Ser at $Asn^{79}$, $Asn^{188}$ and $Asn^{313}$, but it has been found that only two of these sites (79, 188) are glycosylated (Boel et al., 1986, Genetics, 1, 363–369). However, even if two possible glycosylation sites can be glycosylated by the homologous strain or a heterologous strain, the degree with which these sites are glycosylated may vary, e.g. according to the producing strain and the growth medium and conditions.

The above *Rhizomucor miehei* enzyme comprises in its active form 361 amino acid residues and has a calculated molecular 5 weight excluding glycosyl moieties of 38,701. The native, homologously expressed enzyme contains about 6% carbohydrate. In accordance with the invention it is preferred that essentially all of the glycosyl moieties initially present in *Rhizomucor miehei* aspartic protease are removed, although it 10 is expected that an enhancement of the milk clotting activity of such an enzyme will be found at lower degrees of glycosyl removal. Thus, the method according to the invention will preferably result in at least 10% deglycosylation, such as at least 20%. In more preferred embodiments, at least 50% of the glycosyl groups are removed such as least 75%.

The skilled person will, based on the teachings herein and his general knowledge, know how to select the appropriate conditions for treating a glycosylated coagulant to an extent where the milk clotting activity is enhanced as defined herein.

It will be understood that deglycosylating enzymes which are useful according to the present invention include any enzyme having the above enzymatic activity. Preferred deglycosylating enzymes include Endo-β-acetylglucosaminidases (endoglycosidases) having as a common property that they hydrolyze the di-N-acetylchitobiose unit of oligosaccharides attached to asparagine residues in glycoproteins and glycopeptides. Presently known examples of such enzymes include Endo $C_1$ and $C_2$ from *Clostridium perfringens*, Endo D from *Diplococcus pneumoniae*, Endo F from *Flavobacterium meningosepticum*, Endo H (EC 3.2.1.96) from *Streptomyces plicatus* and those from hen oviduct and fig latex. Endo H which is produced in heterologous organisms such as other Streptomyces species or *E. coli* is commercially available.

However, up to now reports disclosing deglycosylation of aspartic proteases by Endo H have related exclusively to laboratory microscale experiments whereas it has been found herein that such enzymes are so enzymatically effective in large scale deglycosylation experiments that a method according to the invention which can be used in an industrial scale is made available for the first time.

The temperature and pH conditions for carrying out the deglycosylation treatment are preferably selected such that the enzymatic activity of the selected enzyme is at an optimum level. The deglycosylating enzyme may suitably be applied in a free form, but it is contemplated that the enzyme may, if desired, also be used in an immobilized form.

The degree of glycosylation of a microbial coagulant prior to and during the deglycosylating treatment may be determined according to well-known methods, such as e.g. the method described by Aikawa et al., supra.

From a production economy point of view it is advantageous that the deglycosylating enzyme selected has a high rate of deglycosylation activity such that the step of deglycosylation is terminated within a short period of time at relatively low amounts of deglycosylating enzyme. Preferably, the deglycosylation step is substantially completed within a period which is at the most a few days such as 1–7 days, although the step is preferably completed within 24 hours and more preferably completed within a period of treatment which is at the most 12 hours. In most preferred embodiments, the period of treatment is at the most 6 hours. It was even found that the treatment may be substantially completed within 1 hour or even within 30 minutes, such as within 15 minutes or even within 10 minutes e.g. within 5 minutes.

In preferred embodiments of the invention, the deglycosylation of a *Rhizomucor miehei* derived aspartic protease is obtained by using a method wherein the ratio between the protease and the deglycosylating enzyme is in the range of 1:10,000 to 1:400,000, including the range of 1:20,000 to 1:250,000 such as e.g. about 1:100,000, 1:25,00 or 1:32,000.

Milk clotting proteases or coagulants which are of microbial origin may, as mentioned above, be derived from a variety of microbial species. Useful microbial coagulants are produced by several fungal species including the above-mentioned *Rhizomucor miehei* and *Rhizomucor pusillus* and by several bacterial species including as examples Bacillus species such as *Bacillus subtilis*. Other examples of fungal species which are potentially useful sources of microbial coagulants include *Endothia parasitica*, Rhizopus species and Physarum species.

For the purposes of this invention, a preferred milk clotting protease is an aspartic protease derived from *Rhizomucor miehei*.

Although microbial coagulants being produced by homologous strains, i.e. strains naturally producing the milk clotting enzymes, have been commercially available for more than 25 years, including the above-mentioned Rennilase® product, the possibility to enhance the milk clotting activity of such naturally produced enzymes significantly as it is disclosed herein has not been suggested up to now. Accordingly, in one industrially interesting embodiment, there is provided a method of enhancing the milk clotting activity of a *Rhizomucor miehei* aspartic protease coagulant which is a homologous enzyme.

As also mentioned above, it may be advantageous to produce microbial coagulants in a heterologous organism, one advantage being that it may thereby be possible to obtain the enzyme in preparation forms which are less contaminated than the natively produced coagulants with other proteins including proteolytic enzymes. Although such contaminating proteins may be at least partially removed by known, appropriate purification processes, such a purification step adds considerably to the production costs. Therefore, in a further interesting embodiment the present invention provides a method as defined herein, wherein the *Rhizomucor miehei* coagulant is one which is expressed in a different, i.e. a heterologous microbial strain.

Such a heterologous microbial production strain for *Rhizomucor miehei* aspartic protease can be selected from a fungal species, a yeast species and a bacterial species. It will be appreciated by the skilled person that any species for which it is known that it can, by appropriate gene technology methods which are known per se, be recombined to express a heterologous protein, can be used. Thus, a suitable host organism for the heterologous coagulant expression system may be a gram positive bacterium, such as a lactic acid bacterial species e.g. Lactococcus and Lactobacillus, or a gram negative bacterial species including *E. coli*. Furthermore, yeast species including as examples Saccharomyces species, Rhodotorula species, Torulopsis species and Kluyveromyces species are of potential interest in this context. Particularly interesting producers of heterologous microbial coagulants are filamentous fungal species such as Aspergillus species including *Aspergillus oryzae* or *Aspergillus niger*. In the present context, further interesting fungal species include Rhizomucor species including *Rhizomucor miehei* and *Rhizomucor pusillus*, Neurospora species, Mucor species and Penicillium species.

For the purposes of the present invention, a preferred heterologous production strain is an *Aspergillus oryzae* strain.

When the gene coding for a microbial coagulant is being expressed in a heterologous organism it is from a production economy point of view extremely important that the milk clotting enzyme is expressed in large amounts in the recombinant heterologous production strain. Accordingly, it is a critical consideration that a production strain is constructed such that the gene coding for the coagulant is under the control of a strong regulatable or constitutively functioning promoter which is functional in the strain. A suitable promoter can be one which is natively associated with the gene in question, but it may also be advantageous to use a promoter naturally occurring in the heterologous strain. Accordingly, in one useful embodiment of the invention the gene coding for the coagulant is under the control of a promoter natively occurring in the heterologous microbial strain.

The skilled person will immediately recognize that the gene coding for the heterologous microbial coagulant can be introduced into the production host strain by transforming a cell hereof with a plasmid carrying the gene or by inserting the gene into the chromosome of the strain e.g. by means of a transposable element.

In preferred embodiments of the invention the deglycosylation treatment of an initially glycosylated parent microbial coagulant results in an enhancement of the milk clotting activity which is at least 10% such as at least 15%. Preferably this enhancement is at least 20%, more preferably at least 30%, most preferably at least 40% and in particular at least 50%. However, it is contemplated that the milk clotting activity enhancement can be even higher such as at least 60% e.g. at least 75% or even at least 100%.

It has been found that the milk clotting performance of a microbial coagulant, when deglycosylated in accordance with the present invention, is improved, not only with regard to its milk clotting activity, but also with regard to an improved milk clotting specificity, i.e. the ratio between the general proteolytic activity of the deglycosylated enzyme and its milk clotting activity is decreased. A higher specificity as defined herein will result in a more efficient cheese manufacturing process when using a coagulant prepared in accordance with the present invention.

In this connection, it has specifically been found that an Endo H treatment of both homologous and heterologous *Rhizomucor miehei* aspartic protease improves the above ratio at least in the order of a range of 5–50%, such as a range of 20–30%, e.g. about 10%.

Furthermore it was found that the deglycosylated milk clotting enzyme prepared according to the invention has a higher degree of thermolability which is considered an advantageous characteristic for a milk clotting enzyme.

An important characteristic for a milk clotting enzyme is that its MCA does not depend to any significant degree on the particular pH in the milk. This may e.g. be expressed as activity ratio at 2 pH values within the relevant pH range which is 6–7. Thus, as an example, a suitable milk clotting enzyme should ideally have an activity ratio similar to or close to that of pure calf chymosin for milk clotting activity at two different pH values such as 6.0/6.5 or 6.5/7.0. Pure (100%) calf chymosin has a pH 6.0/6.5 activity ratio of 0.85.

Thus, it was found during the experimentation leading to the present invention that treatment of certain *Rhizomucor miehei* aspartic proteases having a relatively high pH dependency (i.e. activity ratios above that of calf chymosin) with Endo H reduced the pH 6.0/6.5 or the 6.5/7.0 activity ratios to values closer to that of calf chymosin. The order of this reduction was typically (pH 6.0/6.5) in the range of 10–30%, e.g. from 1,34 to 1.12 (17% reduction) for Modilase® or from 1.02 to 0.81 (21% reduction) for Hannilase®. Accordingly, the method according to the invention is preferably one wherein the resulting deglycosylated enzyme has a low pH dependency as defined above.

It is assumed that the above method of providing a more effective milk clotting enzyme will be useful for preparing other enzymes having different enzymatic activities. Enzymes which can be improved in accordance with this method include proteases, carbohydrate degrading enzymes, nucleases and lipases.

As mentioned above, the present invention provides in a further aspect a microbial coagulant which relative to its parent form is less glycosylated, the milk clotting activity of which is at least 10% higher than that of the parent enzyme. Such a coagulant can be obtained by the above method, or by any method which leads to the desired degree of deglycosylation. It is contemplated that chemical and/or physical treatments of a glycosylated microbial coagulant can be applied as well as the above enzymatic method.

In accordance with the invention, a coagulant as defined above may be derived from microbial species selected from a fungal and a bacterial species, including the species mentioned hereinbefore e.g. Rhizomucor miehei, *Rhizomucor pusillus, Endothia parasitica*, a Rhizopus species, a Physarum species a Penicillium species and a Bacillus species.

However, in accordance with the present invention a preferred coagulant is a *Rhizomucor miehei* aspartic protease.

In interesting embodiments of the invention, the coagulant is a homologous enzyme or it is a coagulant which is produced in a heterologous microbial strain as it has been explained hereinbefore, the production strain preferably being selected from the group consisting of a fungal species including Aspergillus species such as e.g. *Aspergillus oryzae* or *Aspergillus niger*, a yeast species and a bacterial species, *Aspergillus oryzae*, however, being the preferred species.

In accordance with what is explained above, the coagulant according to the invention can in preferred embodiments be a milk clotting enzyme which relative to its parent microbial coagulant has an enhanced milk clotting activity which is at least 15%. Preferably this enhancement is at least 20%, more preferably at least 30%, most preferably at least 40% and in particular at least 50%. However, it is contemplated that the milk clotting activity enhancement can be even higher such as at least 60% e.g. at least 75% or even at least 100%.

In particularly interesting embodiments, the coagulant according to the invention is derived from a *Rhizomucor miehei* coagulant.

In accordance with the invention there is furthermore provided a milk clotting composition comprising the coagulant as defined herein and at least one additive which e.g. may be selected from a salt such as an alkaline metal salt or an earth alkaline metal salt such as e.g. NaCl. NaCl is typically added as a means of preserving the composition against microbial deterioration or degradation of the enzymatic activity. In accordance with the invention the composition may be provided commercially as a liquid composition or as a dry composition, e.g. having a water content of at the most 20%.

The present invention pertains, as it is also mentioned above, in a still further aspect to the use of a coagulant as defined herein for manufacturing cheese. Generally, the coagulant according to the invention can be used in the same manner as a corresponding conventional coagulant product, i.e. the conditions under which the milk clotting activity is optimal are essentially the same for a conventional coagulant and a coagulant which is modified in accordance with the invention. However, it will be understood that the amount of the deglycosylated enzyme required to obtain a certain desired milk clotting activity can be reduced proportionate to the degree of milk clotting activity enhancement caused by the deglycosylation method according to the invention. Alternatively, the microbial coagulant according to the invention can, if desired, be added to the milk in the same amounts as a conventional non-deglycosylated coagulant in which case the rate of milk clotting is increased.

As mentioned above, the present invention also provides a method of producing a microbial coagulant, in particular a *Rhizomucor miehei* derived aspartic protease which, when expressed in a homologous species, is in a glycosylated form, but which, when it is expressed in a recombinant heterologous microbial strain is substantially without glycosylation or glycosylated to such a lower extent relative to the naturally occurring strain that the milk clotting activity of such less glycosylated forms of the protease in increased by at least 10%.

Other fungal species, yeast species and bacterial species including gram negative bacterial species such as *E. coli* are examples of heterologous microbial species which can be used to express such non-glycosylated or initially low-glycosylated coagulants.

The invention is illustrated by the following non-limiting examples:

EXAMPLE 1

Milk clotting activity of deglycosylated homologous *Mucor miehei* aspartic protease 1.1. Microbial coagulants used Two commercial liquid *Rhizomucor miehei* coagulant products of the product series MICROLANTT™ marketed by Chr. Hansen A/S, Hørsholm, Denmark were used. The MICROLANT™ microbial rennets are produced by submerged fermentation of a selected strain of *Rhizomucor miehei* naturally producing the active milk clotting protease (EC 3.4.23.23). The enzyme-containing standardized commercial products are marketed under the trade names Hannilase® and Modilase® S. To these commercial products are added salt in amounts of e.g. about 18–20% (w/v) as a means of preservation hereof.

The Hannilase® coagulant product which was used in this Example has a milk clotting activity of about 67 CHU (Christian Hansen units)/ml. This activity corresponds to 195 IMCU/ml. The recommended dosage of Hannilase® for cheese manufacturing is 15–30 ml/100 l of milk. This coagulant is characterized by having an excellent milk coagulation ability and by being stable under milk pasteurization conditions.

Modilase® S as also used in this Example is an oxidized coagulant product derived from the above Hannilase®. It also has a milk clotting activity of about 67 CHU/ml corresponding to 195 IMCU/ml. The recommended dosage of Modilase® S is 17–33 ml/100 l of milk. This coagulant is characterized by being thermolabile under milk pasteurization conditions whereby the whey resulting from the cheese manufacturing process is essentially free from milk clotting activity after pasteurization.

In the experiments of this Example, 4 samples of each of the above Hannilase® and Modilase® products were tested for milk clotting activity (strength):

(i) non-modified commercial product;

(ii) a sample of (i) subjected to treatment with an endoglycosidase (Endo H) preparation containing about 4 mg/ml of endoglycosidase (500 μl of undiluted coagulant sample +50 μl of Endo-H preparation or 500 μl of diluted coagulant sample +4 μl of Endo-H preparation);

(iii) non-modified commercial product which had been desalted by applying it to a PD10 desalting column (Pharmacia) following the instructions of the manufacturer, whereby the salt medium in which the enzyme is dissolved is replaced by a buffer;

(iv) a sample of (iii) subjected to the treatment as under (ii).

1.2. Determination of milk clotting activity

The milk clotting activities (strengths) of the *Rhizomucor miehei* aspartic protease-containing coagulants (rennets) were determined according to analytical procedure AP 001 of Chr. Hansen A/S.

1.3. Assay principle

The strength of an animal derived rennet or a microbial coagulant is determined as the milk clotting activity. Following the addition of diluted coagulant to a standard milk substrate, the milk will flocculate. The milk clotting time is the time period from addition of the coagulant until formation of visible flocks or flakes in the milk substrate. The strength of a coagulant sample is found by comparing the milk clotting time for the sample to that of a standard rennet preparation, a normal.

1.3.1. Standard assay conditions

Substrate: Reconstituted skimmed milk, pH 6.5, adjusted with $CaCl_2$ prepared as follows: 110 g of low heat-spray dried skimmed milk powder is suspended in 1000 ml of 0.05% (w/v) $CaCl_2$. The milk solution is stirred for 30 minutes. The milk substrate is stored at a temperature in the range of 4–25° C. for no longer than 3 hours.

Temperature: 32° C.+0.2° C. in a thermostatic water bath

Enzyme addition: To 9.7 ml of the reconstituted skimmed milk is added 200 µl of enzyme solution sample, diluted to give a clotting time in the range 380 to 500 seconds.

1.3.2. Activity units

According to this standard activity assay, coagulant strength is given in Christian Hansen Units (CHU)/ml using a powdered rennet standard of calf or adult bovine origin. In this Example, a calf standard was used.

1.4. Results

The milk clotting activity of the above four samples of each of the commercial microbial coagulant products were determined in accordance with the assay procedure as also described above. Based on these assay results, the increase of the milk clotting activity of the endo H treated samples (ii) and (iv) relative to the corresponding untreated samples (i) and (iii) was calculated according to the below formula:

% increase of milk clotting activity (MCA)=(activity of Endo H treated sample–activity of non-treated sample/activity of untreated sample×100

TABLE 1

Milk clotting activity (CHU/ml) of Hannilase ® and Modilase ® samples

| Rennet product | Sample | Activity | Increase of MCA, % |
|---|---|---|---|
| Hannilase ®, | (i) | 61.3 | |
| Hannilase ®, | (ii) | 80.0 | 30.5 |
| Hannilase ®, | (iii) | 57.0 | |
| Hannilase ®, | (iv) | 70.0 | 22.8 |
| Modilase ® S, | (i) | 68.7 | |
| Modilase ® S, | (ii) | 92.0 | 33.9 |
| Modilase ® S, | (iii) | 61.0 | |
| Modilase ® S, | (iv) | 85.5 | 40.2 |

These results show that the addition of salt does not affect the milk clotting activity of the two tested microbial coagulant products to any significant degree and furthermore, that the oxidization treatment to which Modilase® has been subjected does not affect the MCA significantly either. However, the most significant results that were evident from the above experimental data are that the Endo H treatment has a dramatically enhancing effect on the milk clotting activity. Thus, the MCA of Hannilase® was increased by about 20–30% and that of Modilase® by about 30–40% by subjecting these enzyme products to treatment with a preparation of a deglycosylating enzyme.

EXAMPLE 2

Milk clotting activity of deglycosylated heterologous *Mucor miehei* aspartic protease-containing coagulant 2.1. Microbial coagulants used A sample of a preparation of the heterologous *Rhizomucor miehei* aspartic protease coagulant Novoren® 50 XL produced by Novo Nordisk, Bagsværd, Denmark was used as basis for preparing the below test samples. Novoren® is produced by submerged fermentation of a recombinant strain of *Aspergillus oryzae* in which an active *Rhizomucor miehei* milk clotting aspartic protease (EC 3.4.23.23) is expressed.

The following test samples of the Novoren® preparation were prepared:

(i) a sample of Novoren® 50 XL to which was added salt at about 18% (w/v);

(ii) a sample of (i) subjected to treatment with Endo H as described in Example 1;

(iii) a sample prepared by desalting a sample of (i) according to the method described in Example 1;

(iv) a sample of (iii) subjected to the above Endo H treatment.

2.2. Determination of MCA

The milk clotting activities (strengths) of the above heterologous microbial coagulant samples (rennets) were determined according to analytical procedure AP 001 of Chr. Hansen A/S as described above.

2.3. Results

The milk clotting activity of the above four samples of heterologous microbial rennet products were determined in accordance with the assay procedure as also described above. Based on these assay results, the increase of the milk clotting activity of the Endo H treated samples (ii) and (iv) relative to the corresponding untreated samples (i) and (iii) was calculated according to the above calculation formula.

TABLE 2

Milk clotting activity (CHU/ml) of Novoren ® based samples

| Rennet product | Sample | Activity | Increase of MCA, % |
|---|---|---|---|
| Novoren ® 50 XL, | (i) | 250.3 | |
| Novoren ® 50 XL, | (ii) | 363.7 | 45.3 |
| Novoren ® 50 XL, | (iii) | 197.5 | |
| Novoren ® 50 XL, | (iv) | 311.5 | 57.7 |

The most significant results that were evident from the above experimental data are that the Endo H treatment has a dramatically enhancing effect on the milk clotting activity. Thus, the MCA of the salted coagulant was increased by about 45% and that of the desalted coagulant by about 58% by subjecting these enzyme samples to a treatment with a preparation of a deglycosylating enzyme.

EXAMPLE 3

The rate of deglycosylation of Hannilase®, Modilase® S and Novoren® 50 XL by Endo H For the below experiments, the following commercial coagulant preparations as defined above were diluted as follows: Hannilase® and Modilase® S 10× to give an estimated milk clotting activity of about 7.7 and 8.8 CHU/ml, respectively, whereas Novoren® 50 XL was diluted 40× to give an estimated activity of about 7.8 CHU/ml.

To 500 µl of dilutions of each enzyme preparation were added 4 µl of the endo-H preparation as described in Example 1 and the milk clotting activity of these mixtures were determined essentially according to the method described in Example 1 with the exemption that 7 ml of standard skimmed milk substrate was used and only 20 µl of the enzyme preparations were added to the substrate. The milk clotting activities of the mixtures of coagulant preparation and endo-H were determined after 1, 4, 5.5, 24, 28, 29.5 and 48 hours, respectively.

It appeared that the milk clotting activity enhancement in all three samples reached a maximum level within the first hour of incubating the mixtures. The results for the first 24 hours are summarized in the below table 3:

TABLE 3

Rate of enhancement of milk clotting activity during treatment with Endo H deglycosylating enzyme, CHU/ml

| | Hours of Endo H treatment | | | | |
|---|---|---|---|---|---|
| Coagulant | 0 | 1 | 4 | 5.5 | 24 |
| Hannilase ® | 63.1 | 79.7 | 81.9 | 84.9 | 81.4 |
| Modilase ® S | 68.4 | 90.5 | 89.4 | 90.4 | 96.1 |
| Novoren ® 50 XL | 231.6 | 367.5 | 363.0 | 362.5 | 383.3 |

These data illustrate that the major enhancement of the milk clotting activity as a result of Endo H treatment generally occurs within the first hour of treatment. Thus, the increase of milk clotting activity after 1 hour of Endo H treatment of Hannilase®, Modilase® S and Novoren® 50 XL, respectively were 26.4%, 30.7% and 56.9%, respectively.

The above experiment was repeated, but samples for determination of milk clotting activity were collected after 2, 5, 10, 16, 25, 30, 35, 45, 50, 55, 60 and 75 minutes, respectively. The results of this experiment revealed that the major proportion of the enhancement of milk clotting activity occurs within the first 5 minutes of incubation of coagulant with the Endo-H preparation.

EXAMPLE 4

Large scale production of deglycosylated *Rhizomucor miehei* coagulants 4.1. Endo H/*Rhizomucor miehei* aspartic protease ratio of about 1:32,000

100 ml volumes of two commercial liquid *Rhizomucor miehei* aspartic protease-containing coagulant products were subjected to treatment with a liquid Endo H preparation containing about 4 mg/ml of Endo H. The enzymatic strengths were measured in terms of IMCU (international milk clotting units)/g of aspartic protease content.

The two coagulants used in these experiments were:

(i) Hannilase® containing about 12.8 mg of *Rhizomucor miehei* aspartic protease per ml and having a strength of about 600 IMCU per ml, corresponding to about 515 IMCU per g.

(ii) Modilase® S containing also containing about 12.8 mg of *Rhizomucor miehei* aspartic protease per ml and having a strength of about 625 IMCU per ml, corresponding to about 535 IMCU per g.

To 100 ml volumes of these coagulant product the following amounts of the Endo H preparations were added: 0, 0.01, 0.02 and 0.05%, respectively and the enzymatic strength were measured on days 3, 10, 18 and 40, respectively. It was found that Endo-H treatment after day 3 did not enhance the strengths of the treated coagulants further and therefore, only strength data for day 3 are shown in the below table 4.

TABLE 4

Strength of Endo H treated coagulants (day 3)

| Coagulant | % Endo H | Strength, IMCU/g | % increase |
|---|---|---|---|
| Hannilase ® | 0.00 | 515 | |
| | 0.01 | 665 | 29 |
| | 0.02 | 672 | 30 |
| | 0.05 | 669 | 30 |
| Modilase ® S | 0.00 | 563 | |
| | 0.01 | 714 | 27 |
| | 0.02 | 758 | 35 |
| | 0.05 | 750 | 33 |

The above results shows that even at the lowest concentration of Endo H a significant enhancement of the enzymatic strengths is achieved. At a concentration of 0.01% Endo H (molecular weight about 40,000) 0.0004 mg of Endo H is added per ml of the coagulant. Since the content of *Rhizomucor miehei* enzyme protein without carbohydrate (molecular weight about 40,000) in the Hannilase® product is 12.8 mg per ml, the ratio between Endo H protein and Hannilase® protein is as low as about 1:32,000.

4.2. Endo H/*Rhizomucor miehei* aspartic protease ratio of about 1:250,000

A further experiment was carried out to test the effect of the above liquid Endo H preparation containing about 4 mg/ml of Endo H and the above Endo H preparation from Sigma under other conditions than those used in the above experiment 4.2. on deglycosylation of Hannilase® and Modilase® S, respectively. Thus, the Endo H preparations were used at a concentration corresponding to a ratio between Endo H and aspartic protease of about 1:250,000.

The experiment with Hannilase® was carried out at a pH of 4.0 and that with Modilase® S at a pH of 4.4. The experiments were run at 30 and 37° C., respectively. In the experiment at 30° C., 100 ml of the aspartic protease compositions were used whereas only 10 ml volumes were used in the experiment at 37° C. Enzyme strengths in terms of IMCU/ml were measured after 1 day for the Modilase® experiment and after 1 and 4 days of reaction for the Hannilase® experiment. However, the results obtained on day 4 were essentially similar to those on day 1 and are therefore not shown.

The results on day 1 are summarized in the below tables 5 and 6:

TABLE 5

Strength of *Rhizomucor miehei* coagulants treated at 30° C. with Endo H (day 1)

| Coagulant | Strength | % increase |
|---|---|---|
| Hannilase ® | 551 | |
| Sigma Endo H | 655 | 19 |
| Endo H, 4 mg/ml | 720 | 31 |
| Modilase ® | 677 | |
| Sigma Endo H | 793 | 17 |
| Endo H, 4 mg/ml | 878 | 30 |

TABLE 6

Strength of *Rhizomucor miehei* coagulants treated at 37° C. with Endo H (day 1)

| Coagulant | Strength | % increase |
| --- | --- | --- |
| Hannilase ® | 551 | |
| Sigma Endo H | 668 | 21 |
| Endo H, 4 mg/ml | 670 | 22 |
| Modilase ® | 677 | |
| Sigma Endo H | 811 | 20 |
| Endo H, 4 mg/ml | 880 | 30 |

EXAMPLE 5

Cheese making characteristics of deglycosylated homologous *Rhizomucor miehei* aspartic protease compositions Comparative cheese making experiments were carried out at the facilities of Dalum Technical School, Dalum, Denmark with the purpose of comparing the suitability of deglycosylated *Rhizomucor miehei* coagulant preparations with that of the corresponding non-deglycosylated protease and a standard calf chymosin rennet preparation.

In one experiment, the following milk clotting (coagulant) preparations were compared:

(i) Chr. Hansen Standard calf chymosin, lot No. 290172/B, strength: 176 IMCU per ml, (ii) Hannilase®, lot No. 496552, strength: 602 IMCU per ml, and (iii) same as (ii) treated with Endo H, strength: 720 IMCU per ml.

Three cheese making vats each containing 200 l of milk was used in the experiment following a conventional procedure for making Danbo cheese. To the three vats, the following amounts of the above 3 types of coagulants were added:

Vat 1 (control 1): 70 ml of standard calf chymosin, corresponding to 0.062 IMCU per ml milk;

Vat 2 (control 2): 17 ml of untreated Hannilase®, corresponding to 0.051 IMCU per ml milk;

Vat 3 (test): 14 ml of Endo-H treated (deglycosylated) Hannilase®, corresponding to 0.050 IMCU per ml milk;

During the cheese making experiments, observation of the milk clotting, curd formation, cutting time and cutting characteristics of the curd and visual appearance of the curd and the whey were made.

It was found that the cheese formation process proceeded normally in all 3 vats, and no deviations from the normal procedure were required. The curds and wheys had satisfactory appearances on day 2 of the experiments in all 3 vats. However, the curd from the test vat to which the deglycosylated coagulant was added had a better appearance than that from the two other vats (controls) and the whey in the test vat had a more clear appearance than the whey in the two control vats. No significant differences between the characteristics of the cheeses from the three vats were found.

A further experiment was carried essentially as described above with the exception that 21 ml of the oxidation treated homologous *Rhizomucor miehei* coagulant preparation, Modilase® S having a strength of 624 IMCU per ml was used in place of the above Hannilase® product as control 2 and 16 ml of a corresponding Endo-H treated preparation of Modilase® S having a strength of 818 IMCU was used as the test coagulant.

The results of this further experiment were similar to those found in the above first comparative experiment.

It could therefore be concluded that the deglycosylated *Rhizomucor miehei* aspartic protease compositions have excellent cheese making characteristics in large scale cheese making processes and apparently, they have the same efficiencies as compositions containing the corresponding non-deglycosylated proteases, even if used in amounts which are about 20–25% lower.

EXAMPLE 6

The effect of Endo-H treatment of *Rhizomucor miehei* aspartic protease on the proteolytic activity of the enzyme 25 ml samples of Hannilase® having a milk clotting strength of about 64 CHU/ml and containing about 103.7 mg *Rhizomucor miehei* protease in total and of Novoren® having a MCA activity of 255 CHU/ml, respectively were treated with 10 μl of one or both of 2 different liquid Endo H preparations: (i) an Endo H preparation containing about 0.4 mg enzyme/ml (about 16 U/ml) and (ii) Endo H from Sigma, containing 1 U/ml, corresponding to 0.025 mg enzyme/ml or 0.00025 mg in 10 μl. Accordingly, the ratio between Sigma Endo H and the *Rhizomucor miehei* protease was about 1:400,000.

The deglycosylation was allowed to run until completion of the deglycosylation reaction. After dilution of the Endo H treated coagulants to a strength of 1 CHU/ml, the samples were subsequently tested for milk clotting activity according to the above method, and for proteolytic activity.

The proteolytic activity was determined by an assay based on addition of equal volumes of the samples to an amount of Hammerstein casein and measuring after incubation for 90 minutes of these reaction mixtures the amount of liberated TCA soluble peptides, in accordance with the method of Lowry.

The proteolytic activity was defined as delta E (750 nm), i.e. the difference between measurements of a blind and test samples at to.

The results are summarized in the below table.

TABLE 7

Proteolytic activity of *Rhizomucor miehei* aspartic protease before and after Endo H treatment

| Sample | Delta E/CHU | Activity index |
| --- | --- | --- |
| Hannilase ® | 0.845 | 100 |
| Hannilase ®, treated with 0.4 mg/ml Endo H | 0.783 | 93 |
| Hannilase ®, treated with Sigma Endo H | 0.775 | 92 |
| Novoren ® | 0.664 | 100 |
| Novoren ® treated 0.4 mg/ml Endo H | 0.559 | 90 |

The results illustrate that the Endo H treatment results in a reduction of the proteolytic activity relative to the milk clotting activity of the order of about 10%, i.e. the ratio between proteolytic activity and milk clotting is improved significantly.

In further similar experiments, improvements of the above ratio which were in the order of 20–30% were observed.

What is claimed is:

1. A method of producing a milk clotting enzyme comprising the steps of (a) fermenting a strain of *Rhizomucor miehei* or *Aspergillus oryzae* to form a fermentation product comprising a glycosylated *Rhizomucor miehei* aspartic protease and other proteins, and (b) subjecting a quantity of the fermentation product to a deglycosylating treatment to form a coagulant preparation comprising an at least partly deglycosylated aspartic protease and said other proteins, said at least partly deglycosylated protease having a milk clotting activity that is at least 10% higher than a milk clotting activity of the glycosylated aspartic protease.

2. A method according to claim 1 wherein the milk clotting activity is enhanced by at least 20%.

3. A method according to claim 1 wherein the protease being subjected to a deglycosylating treatment has been pre-treated by subjecting it to oxidation.

4. A method according to claim 1, wherein the deglycosylating treatment is for a period of at most 24 hours.

5. A method according to claim 1 wherein the deglycosylating treatment comprises reacting the protease with an enzyme having deglycosylating activity.

6. A method according to claim 5 wherein the ratio between the protease and the deglycosylating enzyme is in the range of 1:10,000 to 1:400,000 weight/weight.

7. A method according to claim 1 wherein the quantity of the fermentation product being subjected to the deglycosylating treatment has a NaCl content in excess of 10% by weight.

8. A method according to claim 1 wherein the protease is a homologously produced enzyme.

9. A method according to claim 1 wherein the protease is expressed in *Aspergillus oryzae*.

10. A method according to claim 9 wherein the expression of the protease is under the control of a promoter natively occurring in the *Aspergillus oryzae* strain.

11. The coagulant preparation formed by the method of claim 1.

12. A preparation according to claim 11 wherein the milk clotting activity of the aspartic protease is at least 20% higher than that of the protease from which it is derived.

13. A preparation according to claim 11 comprising an aspartic protease which is derived from a glycosylated protease which is expressed in *Aspergillus oryzae*.

14. A preparation according to claim 11 wherein prior to the deglycosylation treatment the quantity of the fermentation product is subjected to an oxidation treatment whereby the at least partly deglycosylated aspartic protease becomes thermolabile under milk pasteurization conditions such that whey produced with the at least partly deglycosylated aspartic protease is essentially free from milk clotting activity after pasteurization.

15. The coagulant preparation formed by the method of claim 5.

16. The coagulant preparation formed by the method of claim 8.

17. A milk clotting composition comprising the preparation of claim 11 and at least one additive.

18. A composition according to claim 17 wherein the additive is selected from the group consisting of NaCl and $CaCl_2$.

19. A preparation according to claim 11 which has a NaCl content in excess of 10% by weight.

20. A composition according to claim 17 which is a liquid composition.

21. A composition according to claim 17 which is a dry composition having a water content of at the most 20% by weight.

22. A method of manufacturing cheese comprising the steps of adding to milk a milk clotting effective amount of the coagulant preparation of claim 11 and processing a resultant composition to obtain the cheese.

23. A method of manufacturing cheese comprising the steps of adding to milk a milk clotting effective amount of the coagulant preparation of claim 17 and processing a resultant composition to obtain the cheese.

* * * * *